United States Patent [19]

Falk et al.

[11] Patent Number: 5,387,691

[45] Date of Patent: Feb. 7, 1995

[54] 2-(BENZOTRIAZOL-2-YL)-4-ALKYL-6-(2-HYDROXY-3-BENZOYL-6-ALKOXYBENZYL)PHENOLS AND STABILIZED COMPOSITIONS

[75] Inventors: Robert A. Falk, New City; John J. Luzzi, Carmel; Gregory R. Coughlin, Poughkeepsie, all of N.Y.

[73] Assignee: Ciba-Geigy Corporation, Ardsley, N.Y.

[21] Appl. No.: 26,961

[22] Filed: Mar. 5, 1993

[51] Int. Cl.$^6$ ............................................. C07D 249/20
[52] U.S. Cl. ..................... 548/257; 548/259; 548/260; 548/261
[58] Field of Search ............... 548/257, 259, 260, 261

[56] References Cited

U.S. PATENT DOCUMENTS

| | | | |
|---|---|---|---|
| 3,004,896 | 10/1961 | Heller et al. | 167/90 |
| 3,055,896 | 9/1962 | Boyle et al. | 260/249.5 |
| 3,072,585 | 1/1963 | Milionis et al. | 260/22 |
| 3,074,910 | 1/1963 | Dickson, Jr. | 260/45.75 |
| 3,189,615 | 6/1965 | Heller et al. | 260/308 |
| 3,230,194 | 1/1966 | Boyle | 260/45.8 |
| 3,399,237 | 8/1968 | Dressler et al. | 260/591 |
| 3,936,305 | 2/1976 | Hiraishi et al. | 252/300 |
| 4,127,586 | 11/1978 | Rody et al. | 260/308 |
| 4,169,089 | 9/1979 | Minagawa et al. | 524/91 |
| 4,226,763 | 10/1980 | Dexter et al. | 260/45.8 |
| 4,278,589 | 7/1981 | Dexter et al. | 260/308 |
| 4,278,590 | 7/1981 | Dexter et al. | 260/45.8 |
| 4,283,327 | 8/1981 | Dexter et al. | 260/45.8 |
| 4,315,848 | 2/1982 | Dexter et al. | 260/45.8 |
| 4,383,863 | 5/1983 | Dexter et al. | 106/125 |
| 4,675,352 | 6/1987 | Winter et al. | 524/91 |
| 4,681,905 | 7/1987 | Kubota et al. | 524/91 |
| 4,684,679 | 8/1987 | Kubota et al. | 524/91 |
| 4,684,680 | 8/1987 | Kubota et al. | 524/91 |
| 4,853,471 | 8/1989 | Rody et al. | 548/261 |
| 5,108,835 | 4/1992 | Hähnsen et al. | 428/334 |
| 5,124,723 | 6/1992 | Laver | 346/1.1 |
| 5,166,355 | 11/1992 | Leistner et al. | 548/260 |

FOREIGN PATENT DOCUMENTS

| | | |
|---|---|---|
| 0031302 | 7/1981 | European Pat. Off. . |
| 0180991 | 5/1986 | European Pat. Off. . |
| 0415880 | 3/1991 | European Pat. Off. . |

OTHER PUBLICATIONS

CA 84: 59483, Durmis, Czech CS 157761 15 May 1975.
CA 74: 53666, Jezo, Chem. Zvesti 24(2) 139–44, 1970.
Olson, et al., Macromolecules 1990, 23, pp. 3762–3768.
CA 97:24876u, 1982.
CA 90:72870q, 1977.
CA 84:18291q, 1973.
CA 83:207085r, 1973.
CA 83:60596x, 1972.

*Primary Examiner*—Johann Richter
*Assistant Examiner*—Catherine S. Kilby Scalzo
*Attorney, Agent, or Firm*—Luther A. R. Hall; Michele A. Kovaleski

[57] ABSTRACT

2-(Benzotriazol-2-yl)-4-alkyl-6-(2-hydroxy-3-benzoyl-6-alkoxybenzyl)phenols am prepared by reacting a Mannich base of a 2-(2-hydroxy-5-alkylphenyl)-2H-benzotriazole with a 2-hydroxy-4-alkoxybenzophenone. The hybrid products exhibit outstanding efficacy in protecting organic substrates from light-induced deterioration as well as good resistance to loss by volatilization or exudation during the processing of stabilized compositions at elevated temperatures.

14 Claims, No Drawings

2-(BENZOTRIAZOL-2-YL)-4-ALKYL-6-(2-HYDROXY-3-BENZOYL-6-ALKOXYBENZYL)-PHENOLS AND STABILIZED COMPOSITIONS

The instant invention pertains to novel 2-(benzotriazol-2-yl)-4-alkyl-6-(2-hydroxy-3-benzoyl-6-alkoxybenzyl)phenols and compositions stabilized by said compounds.

BACKGROUND OF THE INVENTION

The UV absorbers of the 2H-benzotriazole and benzophenone type have long been known as very effective light stabilizers for a host of organic materials and have enjoyed considerable commercial success.

The description, preparation and uses of the 2H-benzotriazoles UV absorbers are taught in U.S. Pat. Nos. 3,004,896; 3,055,896; 3,072,585; 3,074,910; 3,189,615; 3,230,194; 4,127,586; 4,226,763; 4,278,589; 4,315,848; 4,383,863; 4,675,352; 4,681,905 and 4,853,471.

The description, preparation and uses of the benzophenone UV absorbers are found in a comprehensive review by G. R. Lapin in the "Encyclopedia of Polymer Science and Technology", N. Bikales, editor, John Wiley-Interscience, New York, Vol. 14, 1971, pp 125–148.

In some circumstances, the benzotriazole and benzophenone UV absorbers exhibit limited compatibility with certain substrates, and/or an excessive tendency to exude, sublime or volatilize away during processing of stabilized compositions into sheets, films, fibers or other pellicles when processing must be done at elevated temperatures. Likewise, such compounds may also suffer undue loss by volatilization or sublimation from fabricated structures, particularly thin rims, coatings or fibers, especially when such structures are subjected to elevated temperatures during use.

Attempts have been made to increase compatibility and to reduce volatilization by modifying the structure of the benzotriazole. U.S. Pat. No. 3,230,194 teaches that substitution of a higher alkyl group (tert-octyl) for a lower alkyl group (methyl) improves compatibility and performance of the substituted benzotriazole in polyethylene.

Likewise in U.S. Pat. Nos. 4,278,590; 4,283,327 and 4,383,863, 2-(2-hydroxy-3,5-di-tert-octylphenyl)-2H-benzotriazole is shown to exhibit an excellent combination of compatibility with and/or solubility in numerous polymer substrates along with superior resistance to loss from stabilization during high temperature processing, in end-use applications where coating or films of the stabilized compositions are exposed to ambient weathering and light, and in photographic applications.

U.S. Pat. No. 4,675,352 teaches that liquid benzotriazoles of low volatility are prepared by the alkylation of preformed 2-(2-hydroxy-5-methylphenyl)-2H-benzotriazole.

U.S. Pat. Nos. 3,936,305; 4,681,905; 4,684,680; 4,684,679 and 5,108,835 teach the 2,2'-methylene-bis-[4-hydrocarbyl-6-(benzotriazol-2-yl)phenols]having high molar activities and low volatility.

U.S. Pat. Nos. 3,399,237 and 4,169,089 and Japanese patent applications Sho 53-113849; 57-6470; 49-78692; 50-74579 and 50-86487 teach the corresponding class of low volatility compounds with high molar activities which are the methylene-bis(2-hydroxybenzophenones).

U.S. Pat. No. 5,166,355 describes a process for making 2,2'-methylene-bis-[6-(2H-benzotriazo-2-yl)-4 -hydrocarbylphenol] or 5,5'-methylene-bis-(2-hydroxy-4-alkoxybenzophenone using bis(dialkylamino)methane.

The instant compounds exhibit low volatility and excellent absorption characteristics in a broad ultraviolet range. Their photographic inertness is particularly useful in photographic compositions, especially in protecting color dye images against the harmful effects of ultraviolet light.

OBJECTS OF THE INVENTION

One object of this invention is to provide some novel UV absorbers having superior stabilization efficacy.

Another object of the invention is to provide novel photographic elements protected from the adverse effects of actinic light by the incorporation therein of the instant compounds of this invention.

DETAILED DISCLOSURE

This invention pertains to 2-(benzotriazol-2-yl)-4-alkyl-6-(2-hydroxy-3-benzoyl-6-alkoxybenzyl) phenols and compositions stabilized by said compounds. Such compositions include photographic elements, polymer substrates, coatings, fibers and films. More particularly, the instant invention relates to compounds of formula I

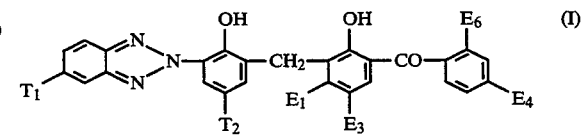

wherein
$T_1$ is hydrogen, chloro, alkyl of 1 to 4 carbon atoms or $-SO_3H$,
$T_2$ is alkyl of 1 to 12 carbon atoms,
$E_1$ is hydrogen, chloro or $-OE_2$,
$E_2$ is hydrogen or alkyl of 1 to 18 carbon atoms,
$E_3$ is hydrogen, alkyl of 1 to 4 carbon atoms, chloro or $-SO_3H$,
$E_4$ is hydrogen, chloro or $-OE_5$,
$E_5$ is hydrogen or alkyl of 1 to 18 carbon atoms, and
$E_6$ is hydrogen, hydroxyl or carboxy.

Preferably, $T_1$ is hydrogen or chloro; most preferably, hydrogen.

Preferably $T_2$ is alkyl of 1 to 12 carbon atoms; most preferably alkyl of 1 to 8 carbon atoms.

Preferably $E_1$ is $-OE_2$ where $E_2$ is hydrogen or alkyl of 1 to 12 carbon atoms; most preferably where $E_2$ is hydrogen or alkyl of 1 to 8 carbon atoms.

Preferably $E_3$ is hydrogen.

Preferably $E_4$ is hydrogen or $-OE_5$ where $E_5$ is hydrogen or alkyl of 1 to 12 carbon atoms; most preferably where $E_5$ is hydrogen or alkyl of 1 to 4 carbon atoms.

Preferably $E_6$ is hydrogen or hydroxyl.

Especially preferred are the compounds where $T_1$ is hydrogen or chloro, $T_2$ is alkyl of 1 to 12 carbon atoms, $E_1$ is $-OE_2$ where $E_2$ is hydrogen of alkyl of 1 to 12 carbon atoms, $E_3$ is hydrogen, $E_4$ is hydrogen or $-OE_5$ where $E_5$ is hydrogen or alkyl of 1 to 12 carbon atoms, and $E_6$ is hydrogen or hydroxyl.

Still more preferred are the compounds where $T_1$ is hydrogen, $T_2$ is alkyl of 1 to 8 carbon atoms, $E_1$ is $-OE_2$ where $E_2$ is alkyl of 1 to 12 carbon atoms, and each of $E_3$, $E_4$ and $E_6$ is hydrogen.

When any of $T_1$ to $E_6$ is alkyl, such groups are, for example, methyl, ethyl, isopropyl, n-butyl, isobutyl, sec-butyl, tert-butyl, tert-amyl, 2-ethylhexyl, isooctyl, tert-octyl, lauryl, tert-dodecyl, tridecyl, n-hexadecyl and n-octadecyl.

The instant invention also pertains to stabilized compositions which comprise (a) an organic material subject to degradation by the imposition of actinic light, and (b) an effective stabilizing amount of a compound of formula I as described supra.

The instant compounds are prepared making a Mannich base of a 2H-benzotriazole having the 3-position on the phenyl ring unoccupied and reacting said Mannich base with a benzophenone. The benzophenones and said 2H-benzotriazoles are largely items of commerce or can be easily prepared by methods known to those of ordinary skill in the art. The instant compounds can also be made by making a Mannich base of the benzophenone and reacting it with an appropriate 2H-benzotriazole.

The instant compounds exhibit good resistance to volatilization, have enhanced solubility in selected solvents, have desirable ultraviolet absorption characteristics and are photographically inert. This combination of properties makes them particularly useful in photographic compositions especially in protecting color dye images against the harmful effects of ultraviolet light.

The instant compounds are useful as ultraviolet absorbers in photographic gelatin layers. The compounds show maximum absorption in the near ultraviolet and sharp cut-off just outside the visible region. The compounds are essentially colorless, are readily dispersed or dissolved by either solvent-dispersion or imbibition methods and are photographically inert.

The instant compounds exhibit excellent compatibility characteristics in the gelatin layers of the photographic composition which lead to compositions essentially without haze coupled with superior protection of the color dye images against the harmful effects of ultraviolet radiation. This combination of properties clearly distinguishes the instant compounds over the closest compounds of the prior art.

Preferably the organic material is a synthetic polymer. Such polymers are especially those containing aromatic moieties such as polystyrene, graft copolymers of styrene such as ABS resins, polyphenylene oxides, polyphenylene sulfides, polyurethanes, polyureas, polyimides, polyamide-imides, aromatic polyesters, polycarbonates, polysulfones, polyethersulfones, polyetherketones, alkyl resins, aminoplast resins and epoxy resins.

Another class of synthetic polymers of especial importance are the polyolefins, such as polypropylene.

In general polymers which can be stabilized include

1. Polymers of monoolefins and diolefins, for example polyethylene (which optionally can be cross-linked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-($\alpha$-methylstyrene).

5. Copolymers of styrene or methylstyrene with dienes or acrylic derivatives, such as, for example, styrene/butadiene, styrene/acrylonitrile, styrene-/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from $\alpha, \beta$-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/-butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).
15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.
16. Polyureas, polyimides and polyamide-imides.
17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.
18. Polycarbonates.
19. Polysulfones, polyethersulfones and polyetherketones.
20. Crosslinked polymers which are derived from aldehydes on the one hand and phenols, ureas and melamines on the other hand, such as phenol/formaldehyde resins, urea/formaldehyde resins and melamine/formaldehyde resins.
21. Drying and non-drying alkyl resins.
22. Unsaturated polyester resins which are derived from copolyesters of saturated and unsaturated dicarboxylic acids with polyhydric alcohols and vinyl compounds as crosslinking agents, and also halogen-containing modifications thereof of low flammability.
23. Thermosetting acrylic resins, derived from substituted acrylic esters, such as epoxy-acrylates, urethane-acrylates or polyester acrylates.
24. Alkyl resins, polyester resins or acrylate resins in admixture with melamine resins, urea resins, polyisocyanates or epoxide resins as crosslinking agents.
25. Crosslinked epoxide resins which are derived from polyepoxides, for example from bis-glycidyl ethers or from cycloaliphatic diepoxides.
26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.
27. Mixtures of polymers as mentioned above, for example PP/EPDM, Polyamide 6/EPDM or ABS, PVC/EVA, PVC/ABS, PVC/HVIBS, PC/ABS, PBTP/ABS.
28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.
29. Aqueous emulsions of natural or synthetic rubber, e.g. natural latex or latices of carboxylated styrene/butadiene copolymers.
30. Polysiloxanes such as the soft, hydrophilic polysiloxanes described, for example, in U.S. Pat. No. 4,259,467; and the hard polyorganosiloxanes described, for example, in U.S. Patent No. 4,355,147.
31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
32. Radiation curable compositions containing ethylenically unsaturated monomers or oligomers and a polyunsaturated aliphatic oligomer.
33. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants 1.1. Alkylated monophenols, for example:
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di -cyclopentyl-4-methylphenol
(α-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated hydroquinones, for example:
2,6-di-tert-butyl-4-methoxyphenol
2,5-di-tert-butyl-hydroquinone
2,5 -di-tert-amyl-hydroquinone
2,6-diphenyl-4-octadecyloxyphenol 1.3. Hydroxylated thiodiphenyl, ethers, for example:
2,2'-thio-bis-(6-tert-butyl-4-methylphenol)
2,2'-thio-bis-(4-octylphenol)
4,4'-thio-bis-(6-tert-butyl-3-methylphenol)

4,4'-thio-bis-(6-tert-butyl-2-methylphenol)

1.4. Alkylidene-bisphenols, for example:
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)butane
2,6-di-(3-tert-butyl-5-methyl-2-hydroxybenzyl)-4-methylphenol
1,1,3-tris-(5-tert-butyl-4-hydroxy-2-methylphenyl)butane
1,1-bis-(5-tert-butyl-4-hydroxy-2-methylphenyl)-3-n-dodecylmercaptobutane ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl]terephthalate.

1.5. Benzyl compounds, for example:
1,3,5-tri-( 3,5-di-ten-butyl-4-hydroxybenzyl)-2,4,6-trimethylbenzene
di-(3,5-di-tert-butyl-4-hydroxybenzyl)sulfide
3,5-di-tert-butyl-4-hydroxybenzyl-mercapto-acetic acid isooctyl ester
bis-(4-ten-butyl-3-hydroxy-2,6-dimethylbenzyl)dithiol terephthalate
1,3,5-tris-(3,5-di-tert-butyl-4-hydroxybenzyl)isocyanurate
1,3,5-tris-(4-tert-butyl-3-hydroxy-2,6-dimethylbenzyl)isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example:
4-hydroxy-lauric acid anilide
4-hydroxy-stearic acid anilide
2,4-bis-octylmercapto-6-(3,5-tert-butyl-4-hydroxyanilino)-s-triazine octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example:

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy-3-methylphenyl)-propionic acid with monohydric or polyhydric alcohols, for example:

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid, for example:
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 1.10 Diarylamines, for example:
diphenylamine, N-phenyl- 1-naphthylamine, N-(4-tert-octylphenyl)- 1-naphthylamine,
4,4'-di-tert-octyl-diphenylamine, reaction product of N-phenylbenzylamine and
2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers 2.1.2-(2.'-Hydroxyphenyl)-benzotriazoles, for example, the 5'-methyl-, 3',5'-di-ten-butyl-, 5-tert-butyl-, 5'-(1,1,3,3-tetramethylbutyl)-, 5-chloro-3',5'-di-tert-butyl-, 5-chloro -3'-tert-butyl-5'-methyl-, 3'-sec-butyl-5'-tert-butyl-, 4-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids, for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyl-dithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone), di-(1-octyloxy-2,2,6,6-tetramethylpiperidin-4-yl) sebacate, di-( 1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperdin-4-yl) imino-hexamethylene-[4-(1-cyclohexyloxy-2,2,6,6-tetramethylpiperidin-4-yl)imino], 2,4,6-tris[N-( 1-cyclohexyloxy-2,2,6,6-tetramethylpiperidin-4-yl)-n-butylamino]-s-triazine.

2.7. Oxalic acid diamides, for example, 4,4'-dioctyloxy-oxanilide, 2,2'-di-octyloxy-5,5'-di-tert-butylox 2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and paramethoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl) 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)phenyl]-6-(4-bromophenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)hydrazine, 3-salicyloylamino- 1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alphaheptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinnamate), di-n-octadecyl 3,5-di-ten-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-ten-butylphenol), 1,3,5-tris(2,6-dimethyl-4-tert-butyl-3-hydroxybenzyl) isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert -butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl -4-hydroxyhydrocinnamamide), calcium his(ethyl 3,5-di-tert-butyl-4-hydroxybenzylphosphonate), ethylene bis[3,3-di(3-tert-butyl-4-hydroxyphenyl)butyrate], octyl 3,5-di-ten-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-ten-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-ten-butyl-4-hydroxybenzyl)isocyanurate, 2,6-di-tert-butyl-p-cresol or 2,2'-ethylidene-bis(4,6-di-tertbutylphenol).

The hindered amine compound of particular interest is selected from the group consisting of bis(2,2,6,6-tetramethylpiperidin-4-yl) sebacate, bis( 1,2,2,6,6-pentamethylpiperidin-4-yl) sebacate, di( 1,2,2,6,6-pentamethyl-piperidin-4-yl) (3,5-di-tert-butyl-4-hydroxybenzyl)-butylmalonate, 4-benzoyl-2,2,6,6-tetramethylpiperidine, 4-stearyloxy-2,2,6,6-tetramethylpiperidine, 3-n-octyl-7,7,9,9-tetramethyl- 1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2]heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylene-bis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis( 1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-2,2,6,6 -tetramethyl-piperidin-4-yl)-amino-s-triazin-2-yl]-1,10-diamino-4,7-diazadecane, mixed [2,2,6,6-tetramethylpiperidin-4-yl/$\beta,\beta,\beta',\beta'$-tetramethyl-3,9-(2,4,8,10-tetraoxaspiro[5.5]-undecane)diethyl]1,2,3,4-butanetetracarboxylate, mixed [1,2,2,6,6-pentamethylpiperidin-4-yl/$\beta,\beta,\beta',\beta'$-tetramethyl-3,9-(2,4,8,10-tetraoxaspiro[5.5]-undecane)diethyl]1,2,3,4-butanetetracarboxylate, octamethylene bis(2,2,6,6-tetramethyl-piperidin-4-carboxylate), 4,4'-ethylenebis(2,2,6,6-tetramethylpiperazin-3-one), N-2,2,6,6-tetramethyl-piperidin-4-yl-n -dodecylsuccinimide, N-1,2,2,6,6-pentamethyl-piperidin-4-yl-n-dodecylsuccinimide, N-1-acetyl-2,2,6,6-tetramethyl-piperidin-4-yl-n-dodecylsuccinimide, 1-acetyl13-dodecyl-7,7,9,9-tetramethyl- 1,3,8-triazaspiro[4.5]decane-2,4-dione, di-(1-octyloxy-2,2,6,6-tetramethylpiperidin-4-yl) sebacate, di-( 1-cyclohexyloxy-2,2,6,6-tetramethyl-piperidin-4-yl)succinate, 1-octyloxy-2,2,6,6-tetramethyl-4-hydroxy-piperidine, poly-{[6-tert-octylamino-s-triazin-2,4-diyl][2-( 1-cyclohexyloxy-2,2,6,6-tetramethylpiperidin-4-yl)imino-hexamethylene-[4-(1-cyclohexyloxy-2,2,6,6-tetramethylpiperidin-4-yl)imino], and 2,4,6-tris[N-(1-cyclohexyloxy-2,2,6,6-tetramethylpiperidin-4-yl)-n-butylamino]-s-triazine.

A most preferred hindered amine compound is bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-ten-butyl-4-hydroxybenzyl)butylmalonate, the polycondensation product of 1-(2-hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis(amino-2,2,6,6-tetramethylpiperidine), N,N',N'',N'''-tetrakis[(4,6-bis(butyl-(2,2,6,6 -tetramethyl-piperidin-4-yl)amino)-s-triazine-2-yl]-1,10-diamino-4,7-diazadecane. di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-ten-octylamino-s-triazin-2,4-diyl][2-(1-cyclohexyloxy-2,2,6,6-tetramethylpiperidin-4-yl) imino-hexamethylene-[4-(1-cyclohexyloxy-2,2,6,6-tetramethylpiperidin-4-yl)imino], or 2,4,6-tris[N-(1-cyclohexyloxy-2,2,6,6-tetramethylpiperidin-4-yl)-n-butylamino]-s-triazine.

The following examples are presented for the purpose of illustration only and are not to be construed to limit the nature or scope of the instant invention in any manner whatsoever.

EXAMPLE 1

2-(2-Hydroxy-3-diethylaminomethyl-5-methylphenyl)-2H-benzotriazole 2-(2-Hydroxy-5-methylphenyl)-2H-benzotriazole (74.3 g, 0.33 tool), diethylamine (37.0 g, 0.51 mol) and paraformaldehyde (17.1 g) are dissolved in 85 mL of n-butanol. The mixture is heated with agitation at reflux (95° to 100° C.) for 44 hours. The solvent is then removed by vacuum distillation to give a yellow viscous liquid as product in high yield (>99%). This Mannich base is identified as the above-named compound by thin layer chromatography using toluene as the mobile phase.

EXAMPLE 2

2-(2-Hydroxy-3-diethylaminomethyl-5-tert-octylphenyl)-2H-benzotriazole 2-(2-Hydroxy-5-tert-octylphenyl)-2H-benzotriazole (70.0 g, 0.22 mol), diethylamine (24.3 g, 0.33 tool) and paraformaldehyde (11.2 g) are dissolved in 55 mL of n-butanol. The mixture is heated with agitation at reflux (95° to 100° C.) for 50 hours. The solvent is then removed by vacuum distillation to give an off-white solid as product in high yield (>99%). This Mannich base is identified as the above-named compound by thin layer chromatography using toluene as the mobile phase.

EXAMPLE 3

2-(Benzotriazol-2-yl)-4-methyl-6-(2-hydroxy-3-benzoyl-6-n-octyloxybenzyl)phenol 2-(2-Hydroxy-3-diethylaminomethyl-5-methyl-phenyl)-2H-benzotriazole (21.0 g, 0.067 mol), 2-hydroxy-4-n-octyloxybenzophenone (22.0 g, 0.067 mol), and p-cymene (80 g) are charged to a reaction flask. The mixture is heated to dissolve, and sodium methoxide (1.0 g, 25% in methanol) is added as catalyst. The solution is heated with agitation under a nitrogen flow at reflux (176°–178° C.) for 24 hours. After cooling to room temperature, the solution is filtered, and the black filtered solid (~1 g) is discarded. The product is then precipitated with methanol. The yellow solid (12.5 g) obtained is vacuum filtered, and identified using thin layer chromatography, with toluene:acetone (1:1) as the mobile phase. To remove the yellow color, the solid product is dissolved in hot toluene, and silica gel is introduced. The silica gel is gravity filtered hot. The toluene is removed by vacuum distillation, yielding 8.2 g of the title compound as an off-white solid, m.p. 124°–126° C. H NMR shows proton resonances at 0.73 ppm, triplet, 3 protons, (terminal —$CH_3$ in —$OC_8H_{17}$); 1.06–1.24 ppm, complex, 8 protons, (inner 4X-$CH_2$ in —$OC_8H_{17}$); 1.32 ppm, quintet, 2 protons, (—$CH_2$ beta to Ar—O); 1.71 ppm, quintet, 2 protons, (—$CH_2$ gamma to Ar—O); 2.32 ppm, singlet, 3 protons (—$CCH_3$); 4.03 ppm, triplet, 2 protons, (—$CH_2$ alpha to Ar-0); 4.24 ppm, singlet, 2 protons, (Ar—$CH_2$—Ar); 6.48 ppm, doublet, 1 proton, ($C_8H_{17}$OCCH—); 6.82 ppm, 1 proton, ($CH_3$CCHC—$CH_2$—Ar); 7.40–7.64 ppm, complex, 6 protons, (Ar—COCCHCH$_3$—, $C_8H_{17}$OCCH—,—NCCHC$_2$H$_2$—); 7.68 ppm, doublet, 2 protons, (AR—COCCHC$_3$H$_3$CH), 7.95 ppm, complex, 2 protons, (—NCCHC$_2$H$_2$CH); 8.05 ppm, 1 proton, (CH₃CCHCNCOH); 11.46 and 12.80 ppm, two singlets, two protons, (exchangeable —OH protons).

Analysis for $C_{35}H_{37}N_3O_4$: Calc: C, 74.5; H, 6.6; N, 7.5. Found: C, 74.0; H, 6.6; N, 7.4.

EXAMPLE 4

2-(Benzotriazol-2-yl)-4-methyl-6-(2-hydroxy-3-benzoyl-6-methoxybenzyl)phenol 2-(2-Hydroxy-3-diethylaminomethyl-5-methylphenyl)-2H-benzotriazole (20.0 g, 0.064 tool), 2-hydroxy-4-methoxybenzophenone (14.7 g, 0,064 mol), and sodium methoxide (1.0 g, 25% in methanol) are charged to a reaction flask. The mixture is heated to 130° C. and held at this temperature for 20 hours with agitation under a nitrogen flow. At that time, the product is identified using thin layer chromatography, with toluene as the mobile phase. To the brown-yellow solid is added hot methanol. The yellow solids are vacuum filtered and triturated twice using methanol, yielding 20.6 g product. To remove the yellow color, the solids are dissolved in hot toluene, and silica gel is introduced. The silica gel is gravity filtered hot. The toluene is removed by vacuum distillation, yielding 12.1 g of the title compound as a pale yellow solid, m.p. 206°–209° C.

H NMR shows proton resonances at 2.32 ppm, singlet, 3 protons, (—CCH₃); 3.89 ppm, singlet, 3 protons, (—OCH₃); 4.27 ppm, singlet, 2 protons, (Ar—CH₂—Ar); 6.54 ppm, doublet, 1 proton, (CH₃OCCH—); 6.76 ppm, singlet, 1 proton (CH₃CCH—CH₂—Ar); 7.48–7.60 ppm, complex, 6 protons (Ar—COCCHCHCHCH—); 7.69 ppm, doublet, 2 protons, (Ar—COCCHC₃H₃CH); 7.95 ppm, complex; 2 protons, (—NCCHC₂H₂CH); 8.06 ppm, singlet, 1 proton, (CH₃CHCNCOH); 11.34 and 12.68 ppm, two singlets, two protons, (exchangeable —OH protons).

Analysis for $C_{28}H_{23}N_3O_4$: Calcd: C, 72.2; H, 5.0; N, 9.0. Found: C, 72.2; H, 4.8; N, 9.8.

EXAMPLE 5

2-(Benzotriazol-2-yl)-4-tert-octyl-6-(2-hydroxy-3-benzoyl-6-n-octyloxybenzyl)phenol Methanol (50 ml) is placed into a 300 ml three-necked flask equipped with a stirrer, thermometer, condenser, Dean-Stark trap and nitrogen inlet. Sodium (0.3 g, 0.013 tool) is added to the methanol and the mixture stirred at room temperature till all the sodium is dissolved. Then, 2-(2-hydroxy-3-diethylaminomethyl-5-tert-octylphenyl)-2H-benzotriazole (10.2 g, 0.025 mol), 2-hydroxy-4-n-octyloxybenzophenone (8.2 g, 0.025 mol) and another 50 ml of methanol are added to the sodium methoxide solution. The reactants are heated at reflux till half the methanol is collected in the Dean-Stark trap. o-Xylene (50 ml) is added and the temperature is raised to the reflux temperature of o-xylene (143°–145° C.) and heating is continued for 24 hours. The mixture is then cooled and acetic acid is added to neutralize the sodium methoxide catalyst. The o-xylene solvent is then removed by vacuum distillation. The crude product obtained is recrystallized from heptane to afford the title compound in a yield of 10 g (62% yield) as a white crystalline solid melting at 96°–100° C.

Analysis for $C_{42}H_{51}N_3O_4$: Calcd: C, 76.2; H, 7.8; N, 6.4. Found: C, 76.6; H, 7.9; N, 6.5.

EXAMPLE 6

2-(Benzotriazol- 2- yl )-4-methyl-6-( 2-hydroxy-3-benzoyl-6-n-octyloxybenzyl)phenol Following the general procedure of Example 5 using the Mannich intermediate of Example 1 and 2-hydroxy-4-n-octyloxybenzophenone, the title compound is obtained as an off-white crystalline solid melting at 128°–130° C.

Analysis for $C_{35}H_{37}N_3O_4$: Calcd: C; 74.6; H, 6.6; N, 7.5. Found: C, 74.7; H, 6.6; N, 7.5.

EXAMPLE 7

2-(Benzotriazol-2-yl)-4-tert-octyl-6-(2-hydroxyl-3-benzoyl-6-methoxybenzyl)phenol Following the general procedure of Example 5 using the Mannich intermediate of Example 2 and 2-hydroxy-4-methoxybenzophenone, the title compound is obtained as a yellow crystalline solid melting at 137°–139° C.

Analysis for $C_{35}H_{37}N_3O_4$: Calcd: C, 74.6; H, 6.6; N, 7.4. Found: C, 74.6; H, 6.7; N, 7.3.

EXAMPLE 8

2-(Benzotriazol-2-yl)-4-tert-octyl-6-(2-hydroxyl-3-benzoyl-6-dodecyloxybenzyl)phenol Following the general procedure of Example 5 using the Mannich intermediate of Example 2 and 2-hydroxy-4-dodecyloxybenzophenone, the title compound is obtained as a yellow crystalline solid melting at 78°–82° C.

Analysis for $C_{45}H_{59}N_3O_4$: Calcd: C, 76.9; H, 8.3; N, 5.9. Found: C, 77.9; H, 8.5; N, 5.9.

EXAMPLE 9

2-(Benzotriazol-2-yl)-4-methyl-6-(2-hydroxy-3-benzoyl-6-dodecyloxybenzyl)phenol Following the general procedure of Example 5 using the Mannich intermediate of Example 1 and 2-hydroxy-4-dodecyloxybenzophenone, the title compound is obtained as a yellow crystalline solid melting at 100°–105° C.

Analysis for $C_{39}H_{45}N_3O_4$: Calcd: C, 75.6; H, 7.3; N, 6.8. Found: C, 75.9; H, 7.6; N, 7.2.

EXAMPLES 10–17

Following the general procedure of Example 5 using the Mannich intermediate of Example 1 or 2 and various substituted benzophenones, the following compounds of formula I are prepared as seen in the Table below. The compounds of Examples 3–9 are also included to make the table complete.

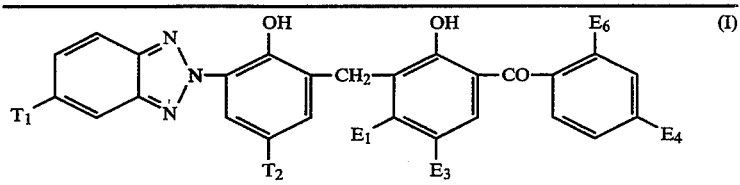

| Example | T₁ | T₂ | E₁ | E₃ | E₄ | E₆ |
|---|---|---|---|---|---|---|
| 3 | H | methyl | n-octyloxy | H | H | H |
| 4 | H | methyl | methoxy | H | H | H |
| 5 | H | t-octyl | n-octyloxy | H | H | H |
| 6 | H | methyl | n-octyloxy | H | H | H |
| 7 | H | t-octyl | methoxy | H | H | H |
| 8 | H | t-octyl | dodecyloxy | H | H | H |
| 9 | H | methyl | dodecyloxy | H | H | H |
| 10 | Cl | methyl | n-octyloxy | H | H | H |
| 11 | H | t-octyl | i-octyloxy | H | H | H |
| 12 | H | methyl | methoxy | SO₃H | H | H |
| 13 | Cl | t-octyl | hydroxy | H | H | H |
| 14 | H | methyl | methoxy | H | methoxy | hydroxy |
| 15 | H | t-octyl | hydroxy | H | hydroxy | hydroxy |
| 16 | H | methyl | methoxy | SO₃H | methoxy | hydroxy |
| 17 | H | t-octyl | methoxy | H | H | hydroxy |

EXAMPLE 18

Thermogravimetric Data

Using a standard thermogravimetric instrument (TA Instruments Model 2950, Thermogravimetric Analyzer), the following isothermal and scanning thermogravimetric data are determined on selected 2H-benzotriazoles, on selected benzophenones and the instant hybrid compounds of this invention. These data are given in the Table below.

| Compound of Example* | Isothermal at 250° C. 100 ml/min N₂ purge Time in minutes to Indicated Weight Loss of Stabilizer | | Scanning at 10° C./min 100 ml/min N₂ purge Temperature °C. at Indicated Weight Loss of Stabilizer | |
|---|---|---|---|---|
| | 10% | 50% | 10% | 50% |
| A | 3.5 | 8.1 | 218 | 260 |
| B | 5.9 | 10.1 | 253 | 295 |
| C | — | <5 | 206 | 247 |
| D | <1 | 11 | 249 | 291 |
| E | (<1) 30 | — | 343 | 386 |
| 3 | (<1) 30 | — | 380 | 419 |
| 4 | (<5) 30 | — | 357 | 405 |

*A is 2-(2-hydroxy-5-methylphenyl)-2H-benzotriazole.
B is 2-(2-hydroxy-5-tert-octylphenyl)-2H-benzotriazole.
C is 2-hydroxy-4-methoxybenzophenone.
D is 2-hydroxy-4-n-octyloxybenzophenone.
E is 2,2'-methylene-bis[4-methyl-6-(benzotriazol-2-yl)phenol].

This instant compounds are certainly more resistant to volatilization and loss under high temperature conditions than are the simple 2H-benzotriazoles and benzophenones. Even the dimeric 2H-benzotriazole described in U.S. Pat. No. 5,166,355 is less resistant to heat loss than are the instant compounds.

EXAMPLE 19

Spectral Properties

The following table shows the absorption maxima and molar extinction coefficients of a number of instant compounds. State-of-the-art commercial benzotriazole and benzophenone UV-absorbers and a number of instant compounds are tested. The concentrations of each of the samples are identical, namely 20 mg/L. The high molar extinction coefficients for the instant compounds allow said compounds to be at lower concentrations while still affording excellent UV light stabilization protection.

| Absorption Maxima and Molar Extinction Coefficients | | | | |
|---|---|---|---|---|
| Compound of | nm | Molar ε | nm | Molar ε |
| A* | 295 | 9,700 | 340 | 15,900 |
| C* | 300 | 30,200 | 342 | 23,700 |
| D* | 294 | 15,700 | 324 | 11,250 |
| Example 3 | 300 | 30,200 | 342 | 23,700 |
| Example 4 | 302 | 39,100 | 340 | 28,000 |

*A is 2-(2-hydroxy-5-methylphenyl)-2H-benzotriazole.
C is 2-hydroxy-4-methoxybenzophenone.
D is 2-hydroxy-4-n-octyloxybenzophenone.

The absorption properties of the instant compounds show that said compounds would provide very effective light stabilization protection to substrates from the deleterious effects of actinic light.

What is claimed is:

1. A compound of formula I

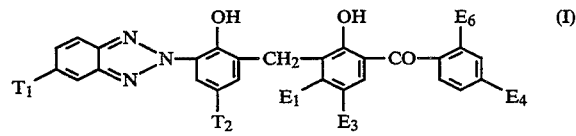

wherein
$T_1$ is hydrogen, chloro, alkyl of 1 to 4 carbon atoms or —SO₃H,
$T_2$ is alkyl of 1 to 12 carbon atoms,
$E_1$ is hydrogen, chloro or —OE₂,
$E_2$ is hydrogen or alkyl of 1 to 18 carbon atoms,
$E_3$ is hydrogen, alkyl of 1 to 4 carbon atoms, chloro or —SO₃H,
$E_4$ is hydrogen, chloro or —OE₅,
$E_5$ is hydrogen or alkyl of 1 to 18 carbon atoms, and
$E_6$ is hydrogen, hydroxyl or carboxy.

2. A compound according to claim 1 wherein $T_1$ is hydrogen or chloro.

3. A compound according to claim 2 wherein $T_1$ is hydrogen.

4. A compound according to claim 1 wherein $T_2$ is alkyl of 1 to 12 carbon atoms.

5. A compound according to claim 4 wherein $T_2$ is alkyl of 1 to 8 carbon atoms.

6. A compound according to claim 1 wherein $E_1$ is $-OE_2$ where $E_2$ is hydrogen or alkyl of 1 to 12 carbon atoms.

7. A compound according to claim 6 wherein $E_1$ is $-OE_2$ where $E_2$ is hydrogen or alkyl of 1 to 8 carbon atoms.

8. A compound according to claim 1 wherein $E_3$ is hydrogen.

9. A compound according to claim 1 wherein $E_4$ is hydrogen or $-OE_5$ where $E_5$ is hydrogen or alkyl of 1 to 12 carbon atoms.

10. A compound according to claim 9 wherein $E_4$ is $-OE_5$ where $E_5$ is hydrogen or alkyl of 1 to 4 carbon atoms.

11. A compound according to claim 1 wherein $E_6$ is hydrogen or hydroxyl.

12. A compound according to claim 1 wherein $T_1$ is hydrogen or chloro, $T_2$ is alkyl of 1 to 12 carbon atoms, $E_1$ is $-OE_2$ where $E_2$ is hydrogen of alkyl of 1 to 12 carbon atoms, $E_3$ is hydrogen, $E_4$ is hydrogen or $-OE_5$ where $E_5$ is hydrogen or alkyl of 1 to 12 carbon atoms, and $E_6$ is hydrogen or hydroxyl.

13. A compound according to claim 12 wherein $T_1$ is hydrogen, $T_2$ is alkyl of 1 to 8 carbon atoms, $E_1$ is $-OE_2$ where $E_2$ is alkyl of 1 to 12 carbon atoms, and each of $E_3$, $E_4$ and $E_6$ is hydrogen.

14. The compound according to claim 1 which is
   (a)  2-(benzotriazol-2-yl)-4-methyl-6-(2-hydroxy-3-benzoyl-6-n-octyloxybenzyl)phenol;
   (b)  2-(benzotriazol-2-yl)-4-methyl-6-(2-hydroxy-3-benzoyl-6-methoxybenzyl)phenol;
   (c)  2-(benzotriazol-2-yl)-4-tert-octyl-6-(2-hydroxy-3-benzoyl-6-n-octyloxybenzyl)phenol;
   (d)  2-(benzotriazol-2-yl)-4-methyl-6-(2-hydroxy-3-benzoyl-6-dodecyloxybenzyl)phenol;
   (e)  2-(benzotriazol-2-yl)-4-tert-octyl-6-(2-hydroxy-3-benzoyl-6-methoxybenzyl)phenol; or
   (f)  2-(benzotriazol-2-yl)-4-tert-octyl-6-(2-hydroxy-3-benzoyl-6-dodecyloxybenzyl)phenol.

* * * * *